US008282915B2

(12) United States Patent
Sayre et al.

(10) Patent No.: US 8,282,915 B2
(45) Date of Patent: *Oct. 9, 2012

(54) TRANSGENIC ALGAE FOR DELIVERING ANTIGENS TO AN ANIMAL (75) Inventors: Richard T. Sayre, Worthington, OH (US); Richard E. Wagner, Bloomington, IN (US); Surasak Siripornadulsil, Columbus, OH (US); Carlos Farias, Casilla (CL)

(73) Assignees: Phyterra Bio Inc., Charlottetown, Prince Edward Island (CA); The Ohio State University, Columbus, OH (US)

( * ) Notice: Subject to any disclaimer, the term of this patent is extended or adjusted under 35 U.S.C. 154(b) by 1139 days.

This patent is subject to a terminal disclaimer.

(21) Appl. No.: 12/145,249

(22) Filed: Jun. 24, 2008

(65) Prior Publication Data

US 2009/0098149 A1 Apr. 16, 2009

Related U.S. Application Data (63) Continuation of application No. 10/311,741, filed as application No. PCT/US01/19643 on Jun. 20, 2001, now Pat. No. 7,410,637.

(60) Provisional application No. 60/212,757, filed on Jun. 20, 2000.

(51) Int. Cl.
*A01N 63/00* (2006.01)
*A61K 39/00* (2006.01)
*C12P 21/06* (2006.01)
*C12N 5/00* (2006.01)
*C12N 15/00* (2006.01)
*C12N 15/82* (2006.01)

(52) U.S. Cl. .................. 424/93.2; 424/93.1; 424/184.1; 435/69.1; 435/320.1; 435/410; 435/468

(58) Field of Classification Search .................. None
See application file for complete search history.

(56) References Cited

U.S. PATENT DOCUMENTS

| | | |
|---|---|---|
| 3,535,421 A | 10/1970 | Briner et al. |
| 3,678,154 A | 7/1972 | Widder |
| 4,776,853 A | 10/1988 | Klement et al. |
| 4,902,508 A | 2/1990 | Badylak et al. |
| 4,992,207 A | 2/1991 | Darnell et al. |
| 5,281,422 A | 1/1994 | Badylak et al. |
| 5,372,821 A | 12/1994 | Badylak et al. |
| 5,484,719 A | 1/1996 | Lam et al. |
| 5,573,784 A | 11/1996 | Badylak et al. |
| 5,654,184 A | 8/1997 | Curtiss, III et al. |
| 5,661,017 A | 8/1997 | Dunahay et al. |
| 5,670,191 A | 9/1997 | Cummings et al. |
| 5,670,349 A | 9/1997 | Cramer et al. |
| 5,679,880 A | 10/1997 | Curtiss, III et al. |
| 5,686,079 A | 11/1997 | Curtiss, III et al. |
| 5,686,125 A | 11/1997 | Mueller |
| 5,744,515 A | 4/1998 | Clapper |
| 5,804,408 A | 9/1998 | Hagiwara et al. |
| 5,821,087 A | 10/1998 | Lowe et al. |
| 5,914,123 A | 6/1999 | Arntzen et al. |
| 5,958,422 A | 9/1999 | Lomonossoff |
| 6,034,298 A | 3/2000 | Lam et al. |
| 6,136,320 A | 10/2000 | Arntzen et al. |
| 6,265,438 B1 | 7/2001 | Steward |
| 6,270,347 B1 | 8/2001 | Webster et al. |
| 6,444,805 B1 | 9/2002 | Sohn et al. |
| 6,805,898 B1 | 10/2004 | Wu et al. |
| 6,932,980 B1 | 8/2005 | Sayre et al. |
| 7,393,999 B1 | 7/2008 | Navarro Acevedo et al. |
| 7,410,637 B2 * | 8/2008 | Sayre et al. .................. 424/93.2 |
| 7,465,784 B2 | 12/2008 | Wang |
| 2002/0167118 A1 | 11/2002 | Billiet et al. |
| 2002/0173033 A1 | 11/2002 | Hammerick et al. |
| 2002/0173213 A1 | 11/2002 | Chu et al. |
| 2003/0022359 A1 | 1/2003 | Sayre et al. |
| 2003/0040809 A1 | 2/2003 | Goldmann et al. |
| 2003/0050711 A1 | 3/2003 | Laurencin et al. |
| 2004/0022806 A1 | 2/2004 | Wikner |
| 2004/0028875 A1 | 2/2004 | Van Rijn et al. |
| 2004/0104672 A1 | 6/2004 | Shiang et al. |

FOREIGN PATENT DOCUMENTS

| | | |
|---|---|---|
| EP | 0108580 A | 5/1984 |
| EP | 0342824 A | 11/1989 |
| EP | 0773295 | 5/1997 |
| EP | 0971034 A | 1/2000 |
| EP | 1114867 A | 7/2001 |
| EP | 1437124 B1 | 7/2004 |
| EP | 1328285 | 3/2006 |
| JP | A-2001240604 | 9/2001 |
| WO | WO 96/11707 A | 4/1996 |
| WO | WO 97/39106 A | 10/1997 |
| WO | WO 99/44573 | 9/1999 |
| WO | WO 99/60838 A | 12/1999 |
| WO | WO 00/73455 | 12/2000 |
| WO | WO 01/98335 | 12/2001 |
| WO | WO 2008/021223 | 2/2008 |

OTHER PUBLICATIONS

Alabi, et al., "The efficacy of immersion as opposed to oral vaccination of *Penaeus indicus* larvae against *Vibrio harveyi*", *Aquaculture*, vol. 178, pp. 1-11 (1999).

Arnon, Daniel I. "Copper Enzymes in Isolated Chloroplasts. Polyphenoloxidase in *Beta vulgaris*", *Plant Physiology*, vol. 24, No. 1, pp. 1-15, (Jan. 1949).

Blowers, A. et al. Studies on *Chlamydomonas* Chloroplast Transformation: Foreign DNA Can Be Stably Maintained in the Chromosome (1989) *The Plant Cell*, vol. 1. pp. 123-132.

(Continued)

*Primary Examiner* — Sumesh Kaushal (57) ABSTRACT

Delivery systems and methods are provided for delivering a biologically active protein to a host animal. The systems and methods provided include obtaining an algal cell transformed by an expression vector, the expression vector comprising a nucleotide sequence coding for the biologically active protein, operably linked to a promoter. In one illustrated embodiment, the biologically active protein is an antigenic epitope and upon administration to the animal the algal cell induces an immune response in the host animal.

22 Claims, 4 Drawing Sheets

OTHER PUBLICATIONS

Blowers, A. et al. "Transcriptional Analysis of Endogenous and Foreign Genes in Chloroplast Transformants of *Chlamydomonas*" (1990) The Plant Cell, vol. 2, pp. 1059-1070.
Brown et al. "Introduction of exogenous DNA into *Chlamydomonas reinhardtii* by electroporation," *Molecular and Cellular Biology*. (1991) vol. 11, No. 4, pp. 2328-2332.
Brown, S., Metal-Recognition by Repeating Polypeptides, *Nature Biotechnology* 15: 269-272 (1997).
Burow et al., "Isolation of cDNA clones of genes induced upon transfer of *Chlamydomonas reinhardtii* cells to low $CO_2$," *Plant Molecular Biology*, 31 (2): 443-448 (1996).
Cai, X. et al., Applications of Eukaryotic Algae for the Removal of Heavy Metals from Water, *Molecular Marine Biology and Biotechnology* 4: 338-344 (1995).
Cai, X. et al., Growth and Heavy Metal Binding Properties of Transgenic *Chlamydomonas* Expressing a Foreign Metallothionein Gene, *Int. J. Phytoremediation* 1: 53-65 (1999).
Cai, X. et al., Heavy Metal Binding Properties of Wild Type and Transgenic Algae (*Chlamydomonas* sp.), *New Developments in Marine Biotechnology*, 189-192 (1998).
Chaney et al. "Phytoremediation of Soil Metals" *Curr. Opin. Biotech.* (1997) vol. 8, pp. 279-284.
Chen, Z. et al. "Cloning and Overexpression of Two cDNAs Encoding the Low-$CO_2$-Inducible Chloroplast Envelope Protein LIP-36 from *Chlamydomonas reinhardtii*" (1997) *Plant Physiol.* vol. 114, pp. 265-273.
Davies et al., Expression of the arylsulfatase gene from the $\beta_2$-tubulin promoter in *Chlamydomonas reinhardtii*, *Nucleic Acids Research*, vol. 20, No. 12, pp. 2959-2965, (1992).
Davies et al., "Sequences controlling transcription of the *Chlamydomonas reinhardtii* $\beta_2$-tubulin gene after deflagellation and during the cell cycle .", *Mol. Cell. Bio.*, 14(8), 5164-5174, 1994.
Debuchy et al., "The argininosuccinate lyase gene of *Chlamydomonas reinhardtii*: an important tool for nuclear transformation and for correlating the genetic and molecular maps of the ARG7 locus",*EMBO Journal*, 8: pp. 2803-2809, (1989).
D'Souza et al., "Effects of monospecific and mixed-algae diets on survival, development and fatty acid composition of penaeid prawn (*Penaeus* spp.) larvae", *Marine Biology*, 133:pp. 621-633, (1999).
Eibl, C. et al. "In Vivo Analysis of Plastid psbA, rbcL and rp132 UTR Elements by Chloroplast Transformation: Tobacco 4 Plastid Gene Expression is Controlled by Modulation of Transcript Levels and Translation Efficiency" (1999) *The Plant Journal* vol. 19(3), pp. 333-345.
Gorman et al.; "Cytochrome F and Plastocyanin: Their Sequence in the Photosynthetic Electron Transport Chain of *Chlamydomonas reinhardi*",P.N.A.S., vol. 54, pp. 1665-1669 (1965).
Gudding et al., "Recent Developments in Fish Vaccinology," *Veterinary Immunology and Immunopathology*, 72, pp. 203-212, (1999).
Haq et al , "Oral immunization with a Recombinant Bacterial Antigen Produced in Transgenic Plants" *Science*, vol. 268, pp. 714-716, (1995).
Harford, C. et al., "Amino Terminal Cu(II)- and Ni(II)-Binding (ACTCUN) Motif of Proteins and Peptides : Metal Binding, DNA Cleavage, and Other Properties," *Acc. Chem. Res.* 30: 123-130 (1997).
Hilleman, M. R. "Current Overview of the Pathogenesis and Prophylaxis of Measles with Focus on Practical Implications" (2002) *Vaccine* vol. 20, pp. 651-665.
Hutchison et al., "Chloroplast transformation", *Molecular Genetics of Photosynthesis*, Chapter 9, pp. 181-196, (1996).
Ishikura et al , "Expression of a foreign gene in *Chlamydomonas reinhardtii* chloroplast", *J Biosci Bioeng.* 87(3):307-314, 1999.
Kagi et al., "Biochemistry of metallothionein," Biochemistry, vol. 27, No. 23, Nov. 15, 1988, pp. 8509-8515.
Kotrba, P. et al., "Enhanced Bioaccumulation of Heavy Metal Ions by Bacterial Cells Due to Surface Display of Short Metal Binding Peptides," *Applied and Enivronmental Microbiology* 65: 1092-1098 (1999).
Mason et al., "Expression of hepatitis B surface antigen in transgenic plants," *Proc. Natl. Acad. Sci.* vol. 89, pp. 11745-11749, (1992).

Mason et al., "Transgenic plants as vaccine production systems," *Tibtech*, vol. 13, pp. 388-392, (1995).
Misra et al. "Heavy metal tolerant transgenic *Brassica napus* L. and *Nicotiana tabacum* L. Plants", *Theor. Appl. Genet.* (1989) vol. 78 pp. 161-168.
Moffat, "Exploring Transgenic Plants as a New Vaccine Source," *Science*, vol. 268, (1995).
Nucifora, G. et al., Cadmium Resistance from *Staphylococcus aureus* Plasmid pI258 cadA Gene Results from a Cadmium-Efflux ATPase, *Proc. Nat. Acad. Sci.* 86: 3544-3548 (1989).
O'Farrell et al., "Differential expression of the virulence-associated protein p57 and characterization of its duplicated gene msa in virulent and attenuated strains of *Renibecterium salmoninarum*" *Diseases of Aquatic Organisms*, 38(2):115-123 (1999).
Patwardhan, A. et al., Phage-Displayed Libraries for the Selection of Optimal Affinity Peptides for Protein Purification Using Ni-Nitrilotriacetic Acid Chromatography, *Biotech. Techniq.* 12: 421-424 (1998).
Patwardhan, A. et al., Selection of Optimum Affinity Tags from a Phage-Displayed Peptide Library: Application to Immobilized Copper(II) Affinity Chromatography, *J.Chromat.* 787: 91-100 (1997).
Piganelli at al., "Evaluation of a whole cell, p57- vaccine against *Renibacterium salmoninarum*" *Diseases of Aquatic Organisms*, 36(I): 37-44 (1999).
Regan, L., Protein Design: Novel Metal-Binding Sites, *TIBS* 20: 280-285 (1995).
Ruffle et al., "Functional Analysis of Photosystem II", *The Molecular Biology of Cholorplasts and Mitochondria in Chlamydomonas*,, Chapter 16, pp. 287-322, (1998).
Scapigliati, G. et al. "The Immune System of Sea Bass, *Dicentrarchus labrax*, Reared in Aquaculture" (2002) *Dev Comp Immuno* vol. 26, pp. 151-160.
Silver, S., Bacterial Resistance ATPases: Primary Pumps for Exporting Toxic Cations and Anions, *Trends. Biol. Sci.* 14: 76-80 (1989).
Shimogawara et al., "High-Efficiency Transformation of *Chlamydomonas reinhardtii* by Electroporation," *Genetics* 148:1821-1828 (1998).
Siripornadulsil S. & Sayre R. pSSCR7: A Transformation Vector for Expression of Foreign Genes in the Nuclear Genome of *Chlamydomonas reinhardtii* poster, presented at the Northeast Algal Society Meeting, Apr. 17, 1099.
Sousa, C. et al., Metalloadsorption by *Escherichia coli* Cells Displaying Yeast and Mammalian Metallothioneins Anchored to the Outer Membrane Protein LamB, *J. Bact.* 180: 2280-2284 (1998).
Tohoyama, H. et al., Resistance to Cadmium is Under the Control of the CAD2 Gene in the Yeast *Saccharomyces cerevisiae*, *Curr. Genet.* 18: 181-185 (1990).
Tsai et al., "Growth Enhancement of Juvenile Striped Mullet by Feeding Recombinant Yeasts Containing Fish Growth Hormone", *The Progressive Fish Culturist*, vol. 56, pp. 7-12, (1994).
Van Muiswinkel, V. B. et al. "The influence of Environmental and Genetic Factors on the Disease Resistance of Fish" (1999) *Aquaculture* vol. 172, pp. 103-110.
Waffenschmidt, S. et al., Isodityrosine Cross-Linking Mediates Insolubilization of Cell Walls in *Chlamydomonas* , Plant Cell 5: 809-820 (1993).
Wiens at al., "Antigenic and functional characterization of p57 produced by *Renibacterium salmoninarum*," *Diseases of Aquatic Organisms*, 37(I): 43-52 (1999).
Wong, M.H. et al., Sludge-Grown Algae for Culturing Aquatic Organisms: Part II. Sludge-Grown Algae as Feeds for Aquatic Organisms, *Envir. Manag.* 20(3) p. 375-389 (1996).
Yoon, K. et al., Regulation of the cadA Cadmium Resistance Determinant of *Staphylococcus aureus* Plasmid pI 258 , *J. Bacteriol.* 173: 7636-7649 (1991).
Bayer Healthcare Pressclub article (Feb. 28, 2005).
California Vet Supply webpage 2 PlaqueOff (downloaded on Jul. 24, 2008) (3 pages).
California Vet Supply webpage PlaqueOff (downloaded on Feb. 10, 2006) (3 pages).
CDA Journal Halitosis webpage (1997).
Critical Reviews in Oral Biology and Medicine 2004.

Dealtime webpage Jason Cosmetics (downloaded on Feb. 10, 2006) (3 pages).
International Dental webpage PlaqueOff (downloaded on Feb. 10, 2006) (4 pages).
News Release Jul. 21, 2008 (2 pages).
News Release Jul. 22, 2008 (2 pages).
News Release Jul. 24, 2008 (1 page).
Plant pathogen interaction Rajamani abstract (2005).
PlaqueOff article (Dec. 17, 2007).
Vitamin Shoppe webpage Jason Cosmetics (downloaded on Feb. 10, 2006) (2 pages).
Wikner et al KI studie Jul. 31, 2008 (8 pages).

* cited by examiner

SEQUENCE LISTING

```
<160> NUMBER OF SEQ ID NOS: 6

<210> SEQ ID NO 1
<211> LENGTH: 13
<212> TYPE: PRT
<213> ORGANISM: Rennibacterium salmoninarum

<400> SEQUENCE: 1

Val Tyr Asn Lys Asp Gly Pro Ala Lys Glu Leu Lys Val
1               5                   10

<210> SEQ ID NO 2
<211> LENGTH: 75
<212> TYPE: DNA
<213> ORGANISM: Rennibacterium salmoninarum
```

-continued

```
<400> SEQUENCE: 2
gatctagatt aaccttcagc tccttggcgg ggccgtcctt gttgtacacg ccccacctt      60 ggtgcgccgt cagag                                                      75

<210> SEQ ID NO 3
<211> LENGTH: 624
<212> TYPE: DNA
<213> ORGANISM: Chlamydomomas reinhardtii

<400> SEQUENCE: 3
atgtcgggct tgaacaagtt catctatgtg ggcctcgtta tctcgcagct gctgactctg      60
gcggcctacg tggtcgtcac ggccggcgct gcccttctgc agaagaaggc gaacacgctc     120
actctgtttg acacccagga gggcattgac aagtacactc ccgtttacaa ggaggtcttc     180
acggcgacca cctacatcat cgcctacccc cagcagcccc agtaccagtt ccagtaccag     240
tggtggatca tccagttcga gctgtttgtg ttcctgctga ccgccgcctg caccgtcttc     300
ccctccatca tcaagcgcat gcgccccgtg gccctgacct tcatcgcctc cgccctggtg     360
ctggtcatgg acaacatcaa cgccatcttc ttcctgctcc gcaacgagac cgccaaggct     420
gtgttcgacg actaccgcat cgccaccgct caggctggcc tgatcatggt tggcgtggcg     480
aacggcctga ccatcttctt cctgggctcg tacgacgctg aggagtcgca tgcgatgccc     540
aacgtgcacg tcacctctga cggcgccacc aaggtgggcg gcgtgtacaa caaggacggc     600
cccgccaagg agctgaaggt gtaa                                            624

<210> SEQ ID NO 4
<211> LENGTH: 501
<212> TYPE: DNA
<213> ORGANISM: Chlamydomomas reinhardtii

<400> SEQUENCE: 4
ggcgccatct aagcagaagg ctgtgggatg tgtcaccgtt aagcatcgga gtttgggaag      60
tagagaatct ggggctgcgg ttttgtggtt tgccgctgcg gtctgcactt ggcagggttg     120
ccccaggtct tggggtgaca gtttagttgc taggttggta gcatgtcctt cgtgacacca     180
gcgcattgca cccgctatgt acattcatcg ttttgggtct ggagcgctgc gcagcacctt     240
tgggtagcga atacttcggg tgagctgctt atctgtatgg tacggatggg cacggctcca     300
agcagcaata cacggacgca catgcaccaa attttggttg tttgagtgga ccggctttat     360
ccaacggttc aggtttggtt gctctctcca tcggaagcag agcagaagca caacacacgt     420
cgcaaacatg attggagcca aggagcatga aatgcgaaag gctggacca tgcacagcgc     480 atgtaataag agtactgcag a                                               501

<210> SEQ ID NO 5
<211> LENGTH: 39
<212> TYPE: DNA
<213> ORGANISM: Artificial
<220> FEATURE:
<223> OTHER INFORMATION: synthetic primer for PCR

<400> SEQUENCE: 5
agcatatggg gcccatgtcg ggcttgaaca agttcatct                             39

<210> SEQ ID NO 6
<211> LENGTH: 75
<212> TYPE: DNA
<213> ORGANISM: Artificial
```

-continued

```
<220> FEATURE:
<223> OTHER INFORMATION: synthetic primer for PCR

<400> SEQUENCE: 6
gatctagatt aaccttcagc tccttggcgg ggccgtcctt gttgtacacg cccccacctt      60
ggtgcgccgt cagag                                                      75
```

TRANSGENIC ALGAE FOR DELIVERING ANTIGENS TO AN ANIMAL

CROSS REFERENCE TO RELATED APPLICATIONS

This application is a continuation application of U.S. patent application Ser. No. 10/311,741, filed on Dec. 18, 2002 now U.S. Pat. No. 7,410,637, a U.S. national counterpart application of international application Serial No. PCT/US01/19643 filed Jun. 20, 2001, which claims priority to U.S. provisional application Ser. No. 60/212,757 filed Jun. 20, 2000.

FIELD OF THE INVENTION

This invention relates to a system for delivering antigens to an animal.

BACKGROUND OF THE INVENTION

Proteins, dipeptide and polypeptide (hereinafter collectively referred to as proteins) are responsible for most of the activities of a cell, such as catalysis, communication, defense, movement, and transport.

Proteins can be delivered to animals for the purpose of activating or supplementing a biological activity. Examples include antigens that activate an immune response and hormones that regulate growth and development.

The bases of a protein's biological activity is its sequence and/or conformation. Hence, the biologically active portion (such as an epitome) should remain essentially intact until it reaches its target destination. Factors that could limit the biological activity of a protein include chemical and enzymatic denaturation, as well as structural barriers that preclude entry into the animal or access to the target destination.

The patent describes a method for producing, and then delivering biologically active proteins to an animal using transgenic algae. The delivery of an antigen to an animal and activation of an immune response is offered as a specific example.

Infectious Disease in Humans

Infectious disease is an age-old problem. Early in human history, infectious diseases such as smallpox, bubonic plague, influenza, measles and many others caused epidemics and countless deaths. More recently, epidemics of Legionnaires' disease, human immunodeficiency virus, Ebola virus, Lyme disease, and others have been significant threats to human health.

Solutions to Infectious Disease

Early in human history, quarantine of infected individuals and improved sanitation measures were used to decrease the spread of infectious disease. Later, chemotherapeutic agents (drugs) were invented and, early on, included chemicals like sulfur and mercury. Modern chemotherapeutics include antibiotics, antiviral drugs, and antiparasitic drugs. Although essential, there are properties of such drugs that are not ideal. For example, drugs do not prevent disease. Rather, drugs are administered after a disease is diagnosed. Another problem is that infectious agents can develop resistance to the drugs such that the drugs are no longer effective against the infectious agents. Finally, drugs can cause serious side affects in the individual to which they are administered.

An alternative to chemotherapeutic agents is administration of immunogenic agents, wherein the immunogens that comprise a composition originating from the infectious agent whose infection one is trying to prevent. After administration, such immunogenic compositions preferably stimulate the immune system such that subsequent infection by the infectious agent is prevented, or disease symptoms caused by the infectious agent are decreased. Such immunogenic compositions are advantageous in that they are administered before the individual contracts the infectious agent. The stimulation of immunity in the individual caused by administration of the immunogenic composition, therefore, is designed to prevent infection and disease. Such immunogenic compositions normally produce few side effects in the individual to which the composition is administered. Finally, infectious agents do not normally develop resistance to immunity that develops as a result of administration of the antigen composition.

Infectious Disease in Non-Human Animals

Infectious diseases in non-human animals also cause significant morbidity and mortality. Such disease is important, not only because non-human animals can sometimes transmit the infectious agents to humans, but also because non-human animals and the products thereof are important human food sources and their loss is economically burdensome.

Infectious Diseases in Aquaculture

An example of an area where infectious non-human animal diseases continue to affect an important human food source is aquaculture. Aquaculture is the farming of aquatic organisms, including fish and other seafood, for human consumption. Currently in the U.S., the domestic fishing industry meets only a small part of the total demand for fish. In 1997, for example, the federal trade deficit for imported fish was nearly $9 billion, the third largest component of the U.S. foreign trade deficit.

In an attempt to meet the demand for fish, the aquaculture industry has responded and, in 1997, produced over $55 billion in farmed fish (statistic from the Food and Agriculture Organization of the United Nations). Furthermore, the aquaculture industry has grown, historically between 10-20% per year for the last ten years. Therefore, it is clear that aquaculture is a rapidly emerging supplement and replacement for the traditional fishing industry and has tremendous growth potential.

One of the major constraints for aquaculture, however, is disease. Under the high density conditions under which fish and other aquatic organisms are farmed, the incidence of infectious disease can be high and, when disease does occur, it can spread rapidly through entire populations with high mortality. On average, 10-30% of farmed fish production, and up to 80% of shrimp production, is lost due to disease (Austin B., et al., 1987 Bacterial Fish Pathogens: Disease in Farmed and Wild Fish, 364 pp Publishers: (Ellis Horwood Ltd., Chichester, UK)).

Solutions to Infectious Diseases in Aquaculture

Again using aquaculture as a specific example, fish diseases with a bacterial etiology can be effectively treated with chemotherapeutic agents from the class called antibiotics. However, as much as 80% of the antibiotic may pass through the fish (Pothuluri, et al., 1998, Res. Dev. Microbiol. 2:351-372), and development of bacteria resistant to the antibiotic may also arise. Such antibiotic-resistant bacterial pathogens can spread, creating entire fish populations harboring pathogenic bacteria that are resistant to the antibiotic. Clearly, it would be advantageous to prevent infection of the fish by the bacteria altogether. Another consideration is that viral and parasitic diseases cannot be treated with antibiotics.

Another strategy for preventing infection and reducing fish losses due to disease is prophylactic administration of an antigen composition, wherein the antigens are derived from an infectious agent, to stimulate the immune system of fish, other aquatic organisms, or other organisms generally (Gudding, et al., 1999, Vet. Immun. Immunopath. 72: 203-212).

Methods of Introducing Antigens into Animals

One problem with antigen compositions, especially in fish, is that many methods for administering them may not be technically or economically practical. For example, direct injection of the antigen composition into fish is labor intensive and is often expensive relative to the future market value of the fish. Furthermore, injection needles can cross-infect fish with contaminating infectious agents, and accidental injection of humans can cause severe infections and anaphylactic reactions. In addition, noninjurious injection of small fish may be difficult.

An alternative route of administration is an oral method wherein the antigen composition is incorporated into the fish food, for example. Another improved method of administering antigens to fish is immersion of the fish for a preset period of time in a suspension of the antigen. However, it can be costly to produce, purify, and package the antigens for such use. Prior art methods of producing antigens have involved the difficulty of growing fish viruses in culture systems to produce enough virus to obtain a sufficient quantity of antigen. In addition, antigen compositions to be administered orally are often encapsulated in expensive polysaccharide-coated beads. Finally, oral administration of antigen compositions have previously shown low and inconsistent levels of stimulation of the fish immune system, thereby minimizing protection against subsequent infection by the infectious agent.

SUMMARY OF THE INVENTION

In accordance with the present invention, a delivery system is provided for delivering peptides to a host animal. The peptides may be growth hormones, antigens derived from a pathogen, other antimicrobial peptides, etc. The delivery system is a transgenic algae that comprises a transgene which comprises a) a polynucleotide encoding at least one peptide, for example an antigenic determinant for the pathogen, and b) a promoter for driving expression of the polynucleotide in the algae. In a preferred embodiment, the transgene further comprises c) a terminator that terminates transcription, and d) all other genetic elements required for transcription. In another preferred embodiment, the transgenic algae further expresses the peptide. If the peptide is an antigenic determinant it is preferably located on the cell surface or within the cytoplasm or an organelle of the transgenic algae. The transgenic algae of the present invention is useful for inducing an immune response in the host animal to the pathogen. The transgenic algae of the present invention is also for treating, ameliorating, or preventing a disease caused by the pathogen.

The present invention also provides methods for delivering the peptide, for example, an antigenic determinant derived from a pathogen, to a host animal. In one aspect, the method comprises orally administering a transgenic algae which comprises (a) a polynucleotide that encodes at least one antigenic determinant of a pathogen for the host animal and (b) a promoter that drives expression of the polynucleotide in the nucleus or an organelle of the algae. Such method is especially useful for delivering the antigenic determinant to a mammal or an aquatic animal. In another aspect, the method comprises immersing the host animal into a suspension comprising water and a transgenic algae which comprises (a) a polynucleotide that encodes at least one antigenic determinant of a pathogen for the host animal, and (b) a promoter that drives expression of the polynucleotide in the nucleus or an organelle of the algae. Such method is especially useful for delivering the antigenic determinant to an aquatic animal.

Thus, in one aspect of the invention, a delivery system is provided for delivering a biologically active protein to a host animal comprising an algal cell transformed by an expression vector, the expression vector comprising a nucleotide sequence coding for the biologically active protein, operably linked to a promoter.

In another aspect of the invention, a delivery system is provided for delivering antigens to a host animal comprising an algal cell transformed by an expression vector, the expression vector comprising a nucleotide sequence coding for an antigenic determinant.

In still another aspect of the invention, a method is provided for inducing an immune response in an animal, comprising the steps of obtaining a transgenic alga expressing an antigenic peptide, administering the transgenic alga to the animal.

Additional features of the present invention will become apparent to those skilled in the art upon consideration of the following detailed description of preferred embodiments exemplifying the best mode of carrying out the invention as presently perceived.

BRIEF DESCRIPTION OF THE FIGURES

The present invention may be more readily understood by reference to the following figures wherein.

DETAILED DESCRIPTION OF THE INVENTION

In one aspect of the present invention provides a delivery system for introducing one or more peptides into a host animal. The delivery system involves the use of is a transgenic algae comprising a transgene which comprises a polynucleotide encoding one or more peptides and a promoter which drives expression of the peptide encoding sequence in the algae.

Antigenic Determinant

The term "antigenic determinant" as used herein refers to a protein or polypeptide which is capable of eliciting an immune response or defense response in the host animal. The antigenic determinant is at least partially derived from a pathogenic microorganism. Herein, the term "microorganism" means a bacterium, virus, fungus, or parasite (i.e., protozoan or helminth, for example). Preferably, the immune response or defense response elicited by the antigenic determinant is protective in the host animal in the sense that a subsequent infection of the host animal by the pathogenic organism from which the antigenic determinant is derived would be prevented, would not cause disease or, if disease were caused, the disease or symptoms associated with the disease would be ameliorated. Preferably, the antigenic determinant itself does not cause disease or any other adverse symptoms in the host animal.

The antigenic determinant is either a holoprotein or a portion of a protein that stimulates the immune system of an animal that is a host for the pathogenic organism. Typically, the antigenic determinants are either secreted by the pathogen or is found on the cell membrane or cell wall thereof, but could potentially be any component of the pathogen. The antigenic determinant may be part of fusion protein. For example, it may be advantageous to fuse the antigenic determinant with a protein that is expressed on the surface of the algal cell.

The transgenic algae of the present invention comprise at least one antigenic determinant of a pathogenic microorganism. In certain embodiments the present transgenic algae comprise a plurality of antigenic determinants from a single microorganism. In other embodiments, the present transgenic algae comprise one or more antigenic determinants from a plurality of pathogenic microorganisms. When expressed, the antigenic determinants may be located in the cytoplasm, in an organelle, particularly the mitochondria or chloroplast, on the cell surface, exported from the cell or in a combination of locations in the algae.

Host Animals

As used herein the term "host animal" refers to all animals capable of mounting an immune or defense response when infected with a pathogenic microorganism. Accordingly, the term host animal, as used herein, encompasses mammals, including humans, companion animals such as cats and dogs, non-companion animals such as cattle and sheep, birds, aquatic vertebrates, and aquatic invertebrates.

Because algae are a food substance for numerous aquatic animals, the transgenic algae of the present invention are especially useful for delivering an antigenic determinant to aquatic vertebrates and invertebrates. Such aquatic vertebrates include, but are not limited to, all vertebrate fish, which may be bony or cartilaginous fish. Such fin-fish include but are not limited to salmonids, carp, catfish, yellowtail, seabream, and seabass.

Immune systems in fish are essentially the same as the immune systems of mammals. The immune system is organized into discrete compartments to provide the milieu for the development and maintenance of effective immunity. Those two overlapping compartments: the lymphoid and reticuloendothelial systems (RES) house the principal immunologic cells, the leukocytes. Leukocytes derived from pluripotent stem cells in the bone marrow during postnatal life include neutrophils, eosinophils, basophils, monocytes and macrophages, natural killer (NK) cells, and T and B lymphocytes. Hematopoietic and lymphoid precursor cells are derived from pluripotent stem cells. Cells that are specifically committed to each type of leukocyte (colony-forming units) are consequently produced with the assistance of special stimulating factors (e.g., cytokines).

Leukocytes, the main cells in the immune system, provide either innate or specific adaptive immunity. These cells are derived from myeloid or lymphoid lineage. Myeloid cells include highly phagocytic, motile neutrophils, monocytes, and macrophages that provide a first line of defense against most pathogens. The other myeloid cells, including eosinophils, basophils, and their tissue counterparts, mast cells, are involved in defense against parasites and in the genesis of allergic reactions. In contrast, lymphocytes regulate the action of other leukocytes and generate specific immune responses that prevent chronic or recurrent infections.

Lymphoid Cells provide efficient, specific and long-lasting immunity against microbes and are responsible for acquired immunity. Lymphocytes differentiate into three separate lines: thymic-dependent cells or T lymphocytes that operate in cellular and humoral immunity, B lymphocytes that differentiate into plasma cells to secrete antibodies, and natural killer (NK) cells. T and B lymphocytes are the only lymphoid cells that produce and express specific receptors for antigens. T Lymphocytes are involved in the regulation of the immune response and in cell mediated immunity and help B cells to produce antibody (humoral immunity). Mature T cells express antigen-specific T cell receptors (TcR) that are clonally segregated (i.e., one cell lineage-one receptor specificity). Every mature T cell also expresses the CD3 molecule, which is associated with the TcR. In addition mature T cells display one of two accessory molecules, CD4 or CD8. The TcR/CD3 complex recognizes antigens associated with the major histocompatibility complex (MHC) molecules on target cells (e.g. virus-infected cell). The TcR is a transmembrane heterodimer composed of two polypeptide chains (usually, alpha and beta chains). Each chain consists of a constant (C) and a variable (V) region, and is formed by a gene-sorting mechanism similar to that found in antibody formation. The repertoire is generated by combinatorial joining of variable (V), joining (J), and diversity (D) genes, and by N region (nucleotides inserted by the enzyme deoxynucleotidyl-transferase) diversification. Unlike immunoglobulin genes, genes encoding TcR do not undergo somatic mutation. Thus there is no change in the affinity of the TcR during activation, differentiation, and expansion.

The activation of B cells into antibody producing/secreting cells (plasma cells) is antigen-dependent. Once specific antigen binds to surface Ig molecule, the B cells differentiate into plasma cells that produce and secrete antibodies of the same antigen-binding specificity. If B cells also interact with Th cells, they proliferate and switch the isotype (class) of immunoglobulin that is produced, while retaining the same antigen-binding specificity. This occurs as a result of recombination of the same Ig VDJ genes (the variable region of the Ig) with a different constant (C) region gene such as IgG. In the case of protein antigens, Th2 cells are thought to be required for switching from IgM to IgG, IgA, or IgE isotypes. IgM is therefore the principal antibody produced during a primary immunization. This primary antibody response is manifested by serum IgM antibodies as early as 3-5 days after the first exposure to an immunogen (immunizing antigen), peaks in 10 days, and persists for some weeks. Secondary or anamnestic antibody responses following repeated exposures to the same antigen appear more rapidly, are of longer duration, have higher affinity, and principally are IgG molecules.

When antibodies bind to antigens, they may 1) neutralize pathogenic features of antigens such as their toxins, 2) facilitate their ingestion by phagocytic cells (opsonization), 3) fix to and activate complement molecules to produce opsonins and chemoattractants (vide infra), or 4) participate in antibody-dependent cellular cytotoxicity (ADCC). In addition to antibody formation, B cells also process and present protein antigens. After the antigen is internalized it is digested into fragments, some of which are complexed with MHC class II molecules and then presented on the cell surface to CD4+ T cells.

In the case of aquatic vertebrates, examples of pathogenic microorganisms whose antigenic determinants may be expressed in the transgenic algae include, but are not limited to *Rennibacterium salmoninarum* (causative agent of bacterial kidney disease in salmon, trout, char and whitefish; i.e., salmonids), *Aeromonas salmonicida*, *Aeromonas hydrophila*, species of *Vibrio* (including *V. anguillarum* and *V. ordalii*), species of *Pasteurella* (including *P. piscicida*), species of *Yersinia*, species of *Streptococcus*, *Edwardsiella tarda* and *Edwardsiella ictaluria*; the viruses causing viral hemorrhagic septicemia, infectious pancreatic necrosis, viremia of carp, infectious hematopoietic necrosis virus, channel catfish virus, grass carp hemorrhagic virus, nodaviridae such as nervous necrosis virus or striped jack nervous necrosis virus, infectious salmon anaemia virus; and the parasites *Ceratomyxa shasta*, *Ichthyophthirius multifillius*, *Cryptobia salmositica*, *Lepeophtheirus salmonis*, *Tetrahymena* species, *Trichodina* species and *Epistylus* species.

Examples of proteins for inducing an immune response in certain aquatic vertebrates include but are not limited to p57 leukocyte agglutinizing protein from *Rennibacterium salmoninarum* and the G-protein from infectious hematopoietic necrosis virus (IHNV).

Aquatic invertebrates which are suitable host animals include, but are not limited to, shrimp, crabs, oysters, and clams.

Shellfish possess a defense system capable of defending against pathogens. This system has many similarities to the nonspecific defense system of vertebrates, such as the activation of phagocytotic cells (hematocytes). However, there is no evidence that shrimp or other invertebrates possess a specific defense response similar to the immune system of vertebrates. Other defense responses activated following infection reported for shrimp include: increases in hematocyte production, production of active oxygen species, activation of phenoloxidase and subsequent melanin synthesis, the production of antimicrobial peptides, encapsulation of the foreign body and coagulation of hematocytes (Rodriquez, et al. 2000, Aquaculture 172:351-372). Unique to invertebrates are specific proteins, such as a beta glucan-binding protein (BGBP) and a lipopolysaccharride-binding agglutinin (LSBA), that recognize cell-wall components of microorganisms and subsequently mobilize hematocytes for phagocytosis (Bachere, E., 2000, Aquiculture 191: 3-11).

Invertebrates have many similarities to the defense response in plants, such as the production of phenolic compounds and reactive oxygen species and the mechanism in which the defense system is activated. The plant-pathogen interaction is a well-characterized signal transduction system composed of nonspecific and specific pathogen elicitors—many the product of an avirulence gene (avr)—and their cognate plant receptors. Following receptor recognition of an elicitor, intracellular mediators orchestrate a cascade response that activates several well-characterized defense mechanisms and, is some cases, short-term acquired immunity mediated by systemically transported signaling molecules. BGBP and LSBA have an analogous role in orchestrating a defense cascade in shrimp that also includes a short-term acquired immunity.

Numerous signaling molecules can activate the defense system of invertebrates, most of which are of pathogen origin. Treatment with dead bacteria or cell wall components, such as B-glucans, lippopolysaccarides, and peptoglycans, have been reported to provide protection against shrimp pathogens when administered prior to challenge. (Alabi, et al. 1999, Aquaculture 178: 1-11) reported that fresh or freeze dried *Vibrio harveyi* administered by immersion, but not orally, reduced infection of *P. indicus* protozoa by *V. harveyi* for 48 hours. More virulent strains increased the level of protection suggesting that the defense response is activated either by different defense eliciting molecules (qualitative) or different numbers of the same defense eliciting molecules (quantitative). Furthermore, tested strains provided cross-protection suggesting that this is a non-specific response. Others have reported that peptoglycan extracted from the cell wall of the nonpathogen *Bifidobacterium thermophilium*, provided protection against vibrosis and white spot syndrome baculovirus when administered orally. These results further support that invertebrates respond to pathogens through a general nonspecific mechanism that can be activated by different elicitor molecules and is effective against a broad range of pathogens. These defense-activating signaling molecules (elicitors) do not result in the production of antibodies. However, for purposes of convenience, the term "antigenic determinant" as used herein also encompasses the elicitors which prompt a defense response in aquatic invertebrates.

Examples of microorganisms which are pathogenic for aquatic invertebrates include, but are not limited to, white spot syndrome virus (WSSV), tuarus virus, IHHNV and *Vibrio harveyii*.

Examples of proteins for inducing an immune response in invertebrates include, but are not limited to, the VP28, VP26c and VP24 proteins of WSSV shrimp virus. See van Hulten et al., Virology 266:227-236 (2000) and WO 0109340 for a discussion of WSSV and its use in vaccines for crustaceans.

Algae

Algae are plant-like organisms without roots, stems or leaves. Algae are distinct from plants in several ways, including phylogenetically, biochemically, and morphologically. Algae contain chlorophyll and vary in size from microscopic forms (phytoplankton) to massive seaweeds. Their habitat is fresh or salt water, or moist places. Most algae are eukaryotic (sub-kingdom=phyciobionta), but several (e.g., cyanobacteria and prochlorophyta) are prokaryotic.

The transgenic algae of the present invention encompass both prokaryotic and eukaryotic algae, which preferably are unicellular. Unicellular algae are also known as microalgae. Preferably, the present transgenic of the present invention algae comprise walls that either lack pores or gaps (referred to hereinafter as "walled" algae) or that contain pores or gaps (referred to hereinafter as "wall-less" algae). Optionally, the wall-less algae are coated with a polysaccharide polymer as described in (Tsai, et al., 1994, Progress. Fish-Culturist 56: 7-12)

The transgenic algae of the present invention comprise a transgene comprising an exogenous polynucleotide which encodes the antigenic determinant and is operably linked to a promoter which drives expression of the exogenous polynucleotide in the algae, and preferably comprises other genetic elements required for expression. Preferably, the transgene comprises a terminator for ending transcription. Also preferably, the transgene is stably integrated into the genomic material found in the nucleus (known hereinafter as a nuclear transformant), the chloroplast (known herein after as a chloroplast transformant), or mitochondria (known hereinafter as a mitochondrial transformant') of the algae. In nuclear transformants, the antigenic determinants preferably are expressed on the cell membrane or cell wall of the transgenic algae or in the cytoplasm thereof.

In certain preferred embodiments, the algae is a green algae (Chlorophyta), a brown algae ((Phaeophyta), or diatoms (Bacillariophyta).

Examples of green algae, which are especially well-suited for use as the delivery system, include members of the

*Chlamydomonas* species, particularly *Chlamydomonas reinhardtii*; the *Chlorella* species, the *Volvox* species, and some marine macrophytes. *Chlamydomonas reinhardtii*, a unicellular eukaryotic green algae is particularly advantageous for use in introducing antigens into animals. *C. reinhardtii* grow vegetatively through mitotic division of haploid cells. Haploid cells are of either the (−) or (+) mating type. When grown in the absence of nitrogen, haploid cells of opposite mating types associate, are held together through their flagella, and eventually fuse to form a diploid zygospore. The diploid zygote undergoes meiosis and releases four haploid cells that resume the vegetative life cycle. One example of a walled green algae is *Chlamydomonas* strain CC-744. One example of a wall-less green algae is *Chlamydomonas* strain CC-425. Both of these strains are available from *Chlamydomonas* Genetic Stock Center, Duke University (Durham, N.C.).

*Chlamydomonas reinhardtii* is particularly preferred because it grows rapidly and is easily and inexpensively grown in culture. Exogenous DNA can easily be introduced into the nuclear, chloroplast, and mitochondrial genome of this algae, and can be expressed at high efficiency ($\geqq$1% of total cellular protein). Auxotrophic mutants (mutants that differ from the wild-type in requiring one or more nutritional supplements for growth) are readily available at the *Chlamydomonas* Genetic Stock Center. Such mutants can be genetically complemented by transformed DNA (i.e., exogenous DNA introduced into the cell), which facilitates selection of algae containing a desired transgene. This selection method is preferred, at it is free from use of antibiotics.

In addition to the ease of growth and genetic manipulation, as cited above, there are additional characteristics of *C. reinhardtii* that make the organism useful for delivering antigens to animals. *C. reinhardtii* is a potential food source for animals, especially larval fish and marine invertebrates (*C. reinhardtii* is nontoxic and nonpathogenic. Both freshwater *C. reinhardtii* and a related marine species, *C. pulsatilla*, are available for administering antigens to aquatic organisms in both environments.

Optionally, the algae of the present invention are genetically engineered such that they will not proliferate unless they are in very specific controlled environments (i.e., such strains will not grow or transfer their genes in the wild). Within the context of this application, such algae are said to be "disabled." Use of such disabled strains inhibits or limits spread of the transgenic algae of the present invention into the environment.

Such disabled strains of algae, particularly strains of *C. reinhardtii*, are constructed by incorporating into the genomes of such strains various genetic mutations that preclude growth and/or mating outside of a specific environment. For example, the transgenic algae may be engineered to contain mutations that prevent photosynthesis. Strains containing such mutations are unlikely to survive in the wild because they cannot produce the energy or reduced carbon necessary to sustain life. Such mutant-containing strains, however, can be grown in the laboratory using acetate as a carbon source. One such type of mutation preventing photosynthesis occurs in, but is not limited to, genes comprising the psbD/psaC operon of *C. reinhardtii*, which is part of the chloroplast genome of the organism. Such mutations in the chloroplast genome are preferably in the chloroplast genome of cells of the (+) mating type. *C. reinhardtii* of the (−) mating type generally do not survive after a mating to produce a diploid cell has occurred (see below).

Other mutations useful in constructing disabled algal strains are mutations in genes resulting in strains that cannot grow in the absence of specific metabolites (i.e., substances produced by, or taking part in, metabolism). Such strains are said to be "auxotrophic" for that particular metabolite. Strains auxotrophic for various amino acids, vitamins, nucleotides, and so forth are particularly useful. For example, some such useful mutations require cells to be grown in the presence of arginine, thiamine, or nicotinamide.

Other mutations that affect the ability of algae to grow and/or transfer its genes, although such mutations are not specifically stated herein, are also included within the scope of this invention.

In one embodiment of this invention multiple mutations of the type described above, for example, are combined into a single strain of algae. Combinations of these mutations in a single strain (also called "stacking" of mutations) result in disabled strains that are particularly nonfunctional in growth and mating. Such strains of algae are particularly unable to grow and transfer their genes in the wild.

Another strategy useful in making disabled algal strains embodied in this invention takes advantage of events that occur naturally in a mating event. In *C. reinhardtii*, when haploid (−) and (+) cells mate to form a diploid cell, only the chloroplast genomes from the (+) mating type organism survive. The chloroplast genomes of (−) mating type cells are degraded during mating. Therefore, *C. reinhardtii* strains in which the transgenes encoding the antigenic determinant are located in the chloroplast genome of a (−) cell are advantageous when control of proliferation of transgenic algae is desired.

Another type of disabled algal strain that is included in this invention are algal strains that have mutations in the genes encoding flagella. For example, in *C. reinhardtii*, flagella are necessary to hold (−) and (+) cells together so that mating can occur. Therefore, certain transgene-containing cells with mutations in genes encoding flagella will be unable to transmit the transgene through mating.

An additional disabling strategy that is part of the present invention is use of the freshwater alga, *C. reinhardtii*, for use in transferring antigens into saltwater aquatic organisms, as *C. reinhardtii* is unable to survive in seawater for more than an hour. *C. reinhardti* strains containing the P5CS gene for proline synthesis can also be used similarly when survival of the algae for longer times is important for a particular application. Strains containing the P5CS gene can tolerate seawater for up to 10 hours before 100% mortality occurs.

Preparation of the Transgenic Algae

In addition to an exogenous polynucleotide encoding an antigenic determinant of a pathogenic microorganism, the transgene which is incorporated into the transgenic algae comprises a promoter which regulates transcription of the exogenous gene in the nucleus, chloroplast, or mitochondria, of the algae, and preferably other genetic elements required for expression. The transgene also preferably includes a terminator for terminating transcription.

To prepare vectors for making the transgenic algae, the exogenous polynucleotide encoding the antigenic determinant is first cloned into an expression vector, a plasmid that can integrate into the algal genome. In such an expression vector, the DNA sequence which encodes the antigenic determinant or a fusion protein comprising the antigenic determinant is operatively linked to an expression control sequence, i.e., a promoter, which directs mRNA synthesis. Preferably, the promoter is an endogenous promoter, i.e., it directs transcription of genes that are normally present in the algae. Examples of suitable promoters for *Chlamydomonas reinhardtii* include, but are not limited to, the chloroplast gene promoter psbA and the nuclear promoter region of the $\beta_2$ tubulin gene. The expression vector, may also contains a ribosome binding site for translation initiation and a transcription terminator. Preferably, the recombinant expression vector also includes an *E. coli* origin of replication and an *E. coli* selectable marker to facilitate cloning of the vector in *E. coli*.

In one embodiment, the exogenous polynucleotide encoding the antigenic determinant is fused to a polynucleotide which encodes a membrane protein to express the antigen on the surface of the cell. For example, the predicted folding topology of the $CO_2$-induced surface protein of *Chlamydomonas reinhardtii* indicates that both the N-terminus and the C-terminus are located on the periplasmic surface of the plasma membrane. Thus, this protein is especially useful for expressing the antigenic determinant on the plasma membrane of *Chlamydomonas reinhardti*.

Plasmids are introduced into the algae by standard transformation methods known to those skilled in the art, such as for example, electroporation, vortexing cells in the presence of exogenous DNA, acid washed beads, polyethylene glycol, and biolistics.

One particular advantage of the present invention is that genes for multiple antigens from one infections agent, or multiple antigens from different infectious agents, can be expressed simultaneously in a single algal cell. Such multiple genes or epitopes can be included in a single vector, for example a plasmid, or in multiple plasmids, each of which must be transformed into the algae. The advantage of such an algae that expresses multiple antigens, is that all of the antigens are introduced into the animal by administration of the particular algal strain to the animal.

Transformation of the algae is determined by assaying for the presence of the gene encoding the antigen by PCR, for example. Procedures known to those of skill in the art, such as for example, deflagellation, copper addition, and ammonium addition of the algae, may be used to enhance expression of the antigenic determinant in the transgenic algae. The choice of such procedure depends upon the promoter used to prepare the construct. See, for example, Davies et al., Nucleic Acids Research 20: 2959-2865 (1992); Dutcher, Current Opinions in Cell Biology 13:39-54 (2001); Moseley et al., Photosynthesis: Mechanisms and Effects.

One type of plasmid vector integrates into the nucleus of algal cells and expresses its proteins which are localized to the cytoplasm of algal cells. One particular vector of this type is pSSCR7, derived from a the plasmid described in Davies (Davies et al. (1994) Plant Cell 6:53-63).

Another type of vector also integrates into the nucleus but expresses proteins that are localized to the periplasm. One particular vector of this type is a derivative of pSSCR7 which has a 5' aryl sulfatase periplasmic targeting transit sequence (Davies et al. (1994) Plant Cell 6:53-63).

A third type of vector integrates into the chloroplast genome by homologous recombination and expresses proteins that are localized to the chloroplasts (Hutchinson, et al., 1996, Chapter 9, Chloroplast transformation. Pgs. 180-196; In: Molecular Genetics of Photosynthesis, Frontiers in Molecular Biology. Anderson B., Salter A H, and Barber J. eds.: Oxford University Press).

Administration of Transgenic Algae to Animals

Animals to which the transgenic algae are administered include, but are not limited to, mammals, birds, and aquaculture species. Aquaculture species include a diversity of species of cultured fin-fish, shellfish, and other aquatic animals. Fin-fish include all vertebrate fish, which may be bony or cartilaginous fish. Such fin-fish include but are not limited to salmonids, carp, catfish, yellowtail, seabream, and seabass. Salmonids are a family of fin-fish which include trout (including rainbow trout), salmon, and Arctic char. Examples of shellfish include, but are not limited to, clams, lobster, shrimp, crab, and oysters. Other cultured aquatic animals include, but are not limited to eels, squid, and octopi.

One method of administering the present transgenic algae to animals is oral delivery of the algae to the animal by feeding. The transgenic algae may be delivered to the animal as a dried cell powder or as a component of the normal diet. For example, in one method of feeding the algae to fish, up to 5% freeze-dried transgenic algae are added to an aqueous mixture containing 5% of a casein-gelatin based protein source. The ingredients are cold-pelleted, freeze-dried, crushed into 2 mm particles, and fed to the fish. Live algae could be delivered in gelatin capsules.

Another method of administering algae to animals, particularly aquatic L animals, is immersion of the host animal in a suspension of live algae. Good results have been obtained by immersing trout in an aqueous suspension containing from between $10^5$-$10^7$ algae per ml of water. Fish were immersed in the suspension anywhere from between 20 seconds to 2 hours, and then removed from the suspension. The immersion method is particularly advantageous for introducing algae into smaller fish (less than about 10 to 15 grams in weight). Such method can be used in combination with oral delivery of algae though feeding, as described above. Other methods of delivery are possible and are within the scope of this invention.

The transgenic algae are introduced into the animal in a regimen determined as appropriate by a person skilled in the art. For example, the transgenic algae may be introduced into the animal multiple times (e.g., two to five times) at an appropriate interval (e.g., every two to three weeks) and dosage or dilution, by normal feeding or by immersion.

EXAMPLES

The following examples are for purposes of illustration only and are not intended to limit the scope of the invention as defined in the claims which are appended hereto. The references cited in this document are specifically incorporated herein by reference.

Example 1

Transgenic Algae Expressing the P57 Immunogen from *Rennibacterium salmoninarum*

*Rennibacterium salmoninarum* is the etiologic agent for bacterial kidney disease, the most common disease of farmed salmonoids. A transgenic algae expressing an antigenic determinant of the fish pathogen. *R. salmoninarum* was prepared using a portion of the P57 leucocyte agglutinizing protein (Genbank accession no. AF123889) of *Rennibacterium salmoninarum* for surface display as an antigen.

A highly antigenic determinant of the P57 protein encoding the amino acids VYNKDGPAKELKV, (SEQ ID NO: 1) residues 112-124, was identified using the program Sciprotein, Scivision (Burlington, Mass.). The following is a synthetic oligonucleotide encoding this peptide and using the codon bias preferred for expression of nuclear genes in the alga *Chlamydomomas reinhardtii*:

(SEQ ID NO. 2)

```
5'- GATCTAGATTAACCTTCAGCTCCTTGGCGGGGCCGTCCTTGTTGT

ACACGCCCCCACCTTGGTGCGCCGTCAGAG -3'
```

The above synthetic oligonucleotide was used to generate a fusion gene between the 3' end of a low $CO_2$-induced plasma-membrane protein gene (Genbank accession no. U31976)

and the P57 antigen encoding sequence creating by adding the above P57 fragment 3' of nucleotide 677 of U31976, shown below:

(SEQ ID NO.: 3)
5'- ATGTCGGGCT TGAACAAGTT CATCTATGTG GGCCTCGTTA

TCTCGCAGCT GCTGACTCTG GCGGCCTACG TGGTCGTCAC

GGCCGGCGCT GCCCTTCTGC AGAAGAAGGC GAACACGCTC

ACTCTGTTTG ACACCCAGGA GGGCATTGAC AAGTACACTC

CCGTTTACAA GGAGGTCTTC ACGGCGACCA CCTACATCAT

CGCCTACCCC CAGCAGCCCC AGTACCAGTT CCAGTACCAG

TGGTGGATCA TCCAGTTCGA GCTGTTTGTG TTCCTGCTGA

CCGCCGCCTG CACCGTCTTC CCCTCCATCA TCAAGCGCAT

GCGCCCCGTG GCCCTGACCT TCATCGCCTC CGCCCTGGTG

CTGGTCATGG ACAACATCAA CGCCATCTTC TTCCTGCTCC

GCAACGAGAC CGCCAAGGCT GTGTTCGACG ACTACCGCAT

CGCCACCGCT CAGGCTGGCC TGATCATGGT TGGCGTGGCG

AACGGCCTGA CCATCTTCTT CCTGGGCTCG TACGACGCTG

AGGAGTCGCA TGCGATGCCC AACGTGCACG TCACCTCTGA

CGGCGCCACC AAGGTGGGCG GCGTGTACAA CAAGGACGGC

CCCGCCAAGG AGCTGAAGGT GTAA-3'

Figure 3:
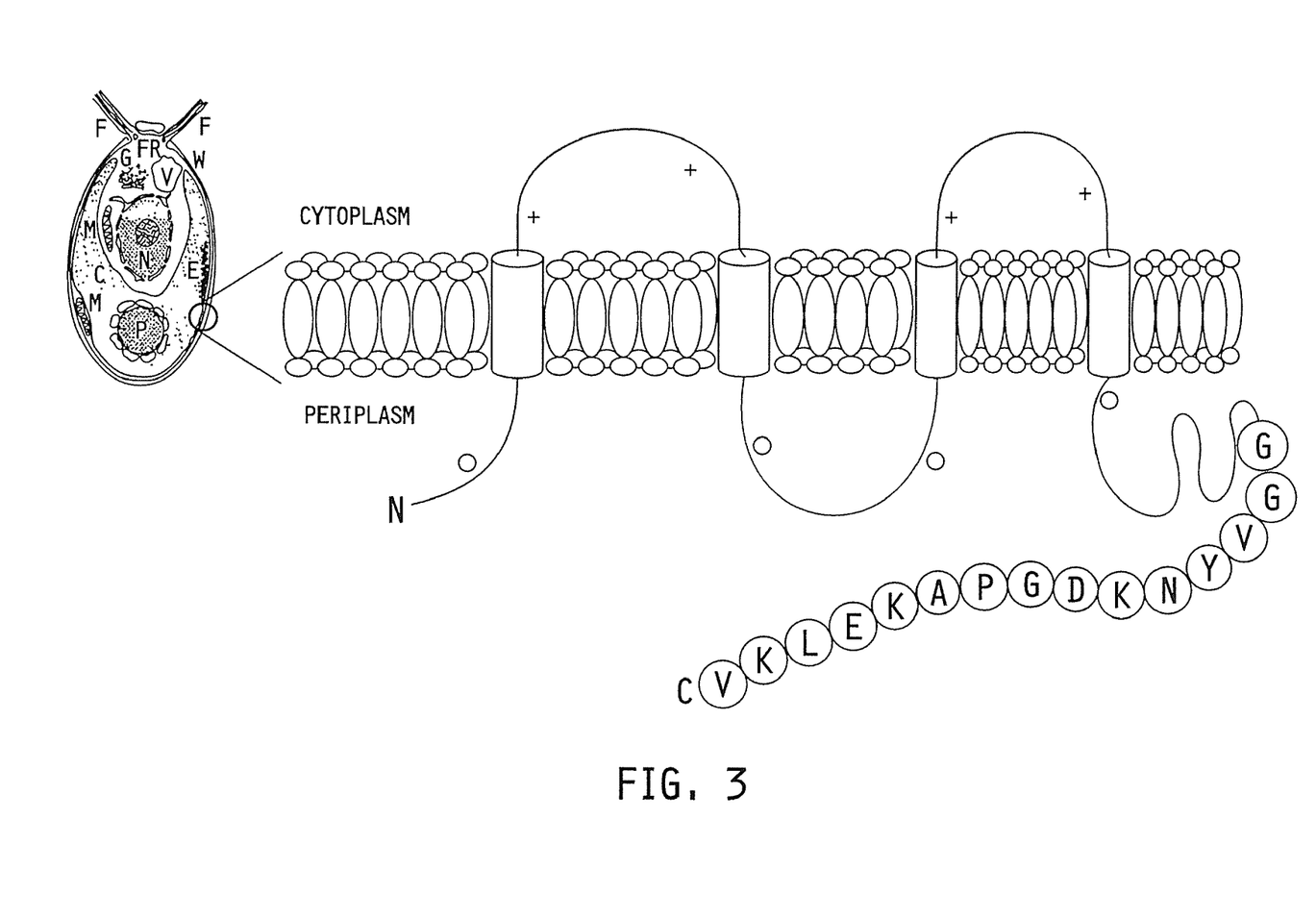
FIG. 3 is a diagram showing the expression between the 3' end of a low $CO_2$-induced plasma-membrane protein gene and a P57 antigen, and showing that the P57 antigen is located on the periplasm side of the cell membrane.

It was expected that the P57 epitope would be expressed on the periplasm side of the cell membrane, as shown in FIG. 3. The gene fusion then was cloned into the multi-cloning site of plasmid pSSCR7 under control of the β₂ tubulin promoter of Chlamydomonas. pSSCR7 was constructed by cloning the HindIII/EcoRI fragment (~2.7 Kbp) that carries the Chlamydomonas β₂-tubulin promoter and the 5' end of arysulfatase gene (~1.0 Kbp) from pJD55 (Davies, 1992 Nucleic Acids Research 20: 2959-2965) into pUC18, and designated as pβ₂TU1. In order to eliminate the 5' end of arysulfatase gene, the β₂-tubulin promoter was amplified by PCR. The PCR product was cloned into the BamHI/EcoRI sites of pUC18 to make plasmid pβ₂TU2. The TATA box was found by DNA sequence analysis ~100 bp away from BamHI site. In order to introduce a unique NdeI site which contains an ATG codon, and a unique NarI site, which was used to clone the 3' terminator, a NdeI site was removed from pUC 18 to make pUN and both sites were removed from pUC18 to make pUNN. A XhoI/Nar fragment containing the 3'-terminator from Chlamydomonas low $CO_2$-induced membrane protein gene, as follows:

(SEQ ID NO. 4)
5'- GGCGCCATCT AAGCAGAAGG CTGTGGGATG TGTCACCGTT

AAGCATCGGA GTTTGGAAG TAGAGAATCT GGGGCTGCGG

TTTTGTGGTT TGCCGCTGCG GTCTGCACTT GGCAGGGTTG

CCCCAGGTCT TGGGGTGACA GTTTAGTTGC TAGGTTGGTA

GCATGTCCTT CGTGACACCA GCGCATTGCA CCCGCTATGT

ACATTCATCG TTTTGGGTCT GGAGCGCTGC GCAGCACCTT

TGGGTAGCGA ATACTTCGGG TGAGCTGCTT ATCTGTATGG

-continued
TACGGATGGG CACGGCTCCA AGCAGCAATA CACGGACGCA

CATGCACCAA ATTTTGGTTG TTTGAGTGGA CCGGCTTTAT

CCAACGGTTC AGGTTTGGTT GCTCTCTCCA TCGGAAGCAG

AGCAGAAGCA CAACACACGT CGCAAACATG ATTGGAGCCA

AGGAGCATGA AATGCGAAAG AGCTGGACCA TGCACAGCGC

ATGTAATAAG AGTACTGCAG A -3' was combined with β₂-tubulin promoter to form expression vector pSSCR1. A KpnI/SstI fragment containing the multi-cloning sites from pBluscript II KS was cloned into pSSCR5 to make the final expression vector, pSSCR7. (FIG. 1.)

Figure 1:
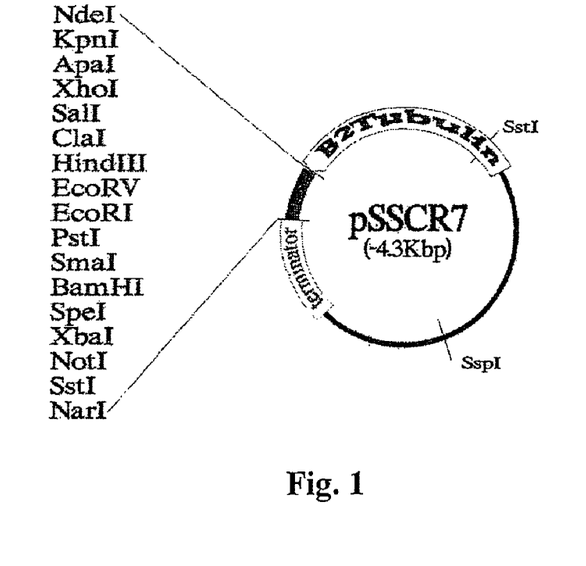
FIG. 1 shows the pSSCR7 plasmid used for constructing nuclear transfection vectors for use in the present invention.

As seen in FIG. 1, the pSSCR7 has sixteen useful cloning sites including NaeI, KpnI, ApaI, XhoI, SalI, ClaI, HindIII, EcoRV, EcoRI, PstI, SmaI BamHI, SpeI, XbaI, NotI and NarI, that can be used for introducing one or more coding sequences, as shown in FIG. 1. The fusion gene described above was cloned into the NdeI and XbaI cites.

The resulting plasmid (pCREpitope) was co-transformed into the nucleus by electroporation into Chlamydomonas reinhardtii strain CC-425 using an equimolar amount of p389, a plasmid containing the Arg-7 gene (see Debuchy et al., EMBO, 1989. Vol 8, 2803-2809). The Arg-7 gene compliments the arginine auxotrophic strain of Chlamydomonas, CC-425 (Debuchy et al., EMBO, 1989. Vol 8, 2803-2809). Transformants were obtained after plating the cells on TAP-agar containing 100 μg arginine per ml of medium. The plates were illuminated with fluorescent tubes at 10 μmol photons/m²/sec at 22-27° C. Transformants were found after 9-10 days of incubation. The resulting transfected algae expressing the fusion protein are known as E-22.

The main features of the new expression vector are (i) the use of the β₂-tubulin promoter, (ii) the construction of sixteen unique cloning sites, (iii) the use of high copy number (in E. coli), pUC18, as the original plasmid, and (iv) the small size of new expression vector (4.4 Kpb).

Figure 2:
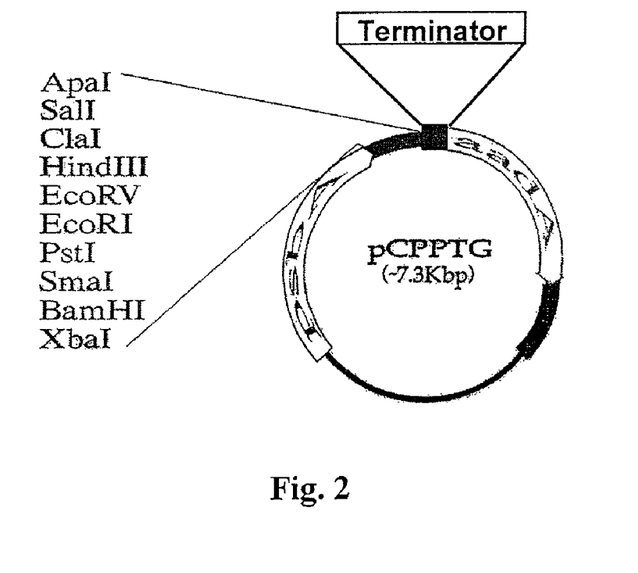
FIG. 2 shows the pCPPTG plasmid used for constructing chloroplast transfection vectors for use in the present invention.

Another plasmid was created by inserting the entire P57 gene into pCPPTG, as shown in FIG. 2. pCPPTG is a plasmid constructed for expression of foreign genes in chloroplasts. It based on a modified E. coli vector, pUC18. As seen in FIG. 2, pCPPTG comprises the psbA promoter, psbA terminator, aadA cassette, and a multicloning site located between the psbA promoter and terminator. The psbA promoter, psbA terminator, and aadA cassette are derived from the pBA155dH3 plasmid, while the multicloning site is derived from pBluescript IIKS (described in Hutchison et al, (1996) Chapter 9, and Ruffle et al, Chapter 16; In Molecular Genetics of Photosynthesis, Frontiers in Molecular Biology. Oxford Univ. Press). The entire P57 gene from R. salmoninarum was cloned into the multicloning site, specifically the ApaI and PmeI sites, of pCPPTG.

Co-transformants growing on medium lacking arginine and containing the membrane protein-P57 fusion were identified by PCR amplification of the membrane protein-P57 fusion gene using the following oligonucleotide primers:

(SEQ ID NO. 5)
Primer
C113-5'- AGCATATGGGGCCCATGTCGGGCTTGAACAAGTTCATCT (SEQ ID NO. 6)
EPITOPE-3'- GATCTAGATTAACCTTCAGCTCCTTGGCGGGGCCGTC

CTTGTTGTACACGCCCCCACCTTGGTGCGCCGTCAGAG

In order to perform PCR on the transformants, total genomic DNA from C. reinhardtii was isolated. To do this, cell cultures (20 ml) were pelleted by centrifugation and resuspended in 0.35 ml TEN buffer. The resuspended cells were incubated with 50 pt of 2 mg/ml proteinase K and 25 µl of 20% SDS for 2 hr at 55° C. Then, 50 µl of 5M potassium acetate was added and the cells were incubated on ice for 30 min. The lysate was extracted by phenol:chloroform and DNA was precipitated by ethanol.

Those cells that were positive for the presence of the membrane protein-P57 fusion product by PCR were then were screened by western blot analysis using antibodies against the intact P57 protein. As demonstrated by western blot analysis (see FIG. 5), antibodies generated against the intact P57 protein recognized the 57 kD P57 protein from solubilized whole cell extracts of transgenic algae (CP57) expressing the P57 protein. No protein was detected on the western blot for non-transformed cells.

Example 2

Immersion

Transgenic *Chlamydomonas reinhardtii* expressing the P57 protein from *Rennibacterium salmoninarum* as a fusion protein on the plasma membrane (called E-22 algae) or in the chloroplast (called CP57 algae) were constructed as described in Example 1. Control algae (the CC-2137 strain of *C. reinhardtii*) were also used to test administration by immersion.

The algae were grown in tris-acetate-phosphate (TAP) medium. See Gorman D S and Levine R P (1965), Proc. Nat. Acad. Sci. 54: 1665-1669, to a density of $1\times10^6$ cells/ml at 22-27° C. with 10 µmol photons/$m^2$/sec illumination from fluorescent tubes. The algal cells were harvested by centrifugation and resuspended in water to a density of approximately $1\times10^6$ cells/ml.

Rainbow trout juveniles (average initial weight, 9.1±0.5 g) were subjected to a bath treatment in water containing algae in a 20 L barrel container (one barrel containing each of the E-22, CP57 and CC-744 algae). Exposure of the trout to the various algae was for 2 hours with intense aeration of the water. The concentrations of the three types of algae were as follows: CP57, $7.97\times10^5$ cells/ml; 2137, $2.71\times10^6$ cells/ml; and E-22, 2.97' $10^6$ cells/ml. A control treatment was also performed where additional fish were handled identically, except that they were not exposed to algae (sham immersion). After immersion, both controls and those immersed in algae, were distributed into 3 tanks per immersion treatment. All the fish groups were fed with the same commercial diet at the rate of 2% of fish weight for 3 weeks (Bioproducts, Inc. Oregon). After that period, the fish were immersed again in a $2^{nd}$ treatment according to the same procedure as in the first treatment. The concentrations of the three algae types for the $2^{nd}$ treatment were as follows: CP57, $1.46\times10^6$ cells/ml; 2137, $6.57\times10^5$ cells/ml; and E-22, $1.23\times10^6$ cells/ml. The fish were fed with the commercial diet for 4 weeks until the second sampling in the experiment (7 weeks) (a first sampling was performed prior to any feeding). All fish were fasted for 24 h prior to treatment.

The water temperature increased gradually from 12 to 17° C. during the course experiment due to seasonal environmental changes. Diurnal light:dark cycle was regulated at 12 h: 12 h. Total fish weight in each tank was measured 3 weeks after the first treatment, and then at 7 and 9 weeks after the first immunization. The fish were kept for the last 2 weeks at the feeding rate of 1.5% of fish weight.

Blood was taken before the initiation of the experiment and at the time of weighing fish (3, 7, and 9 weeks) from caudal vein with heparinized syringe for plasma, and with non-heparinized syringe for serum. Six fish were randomly selected per tank for the determinations of hematocrit, hemoglobin, liver and spleen weights. Mucus from the fish was collected and frozen. Hematocrit was determined by the microhematocrit method. Total hemoglobin was determined with Sigma Diagnostic Kits (procedure No. 525) by using human hemoglobin solution as standard. All procedures and handling of animals were conducted in compliance with the guidelines of the Institutional Laboratory Animal Care and Use Committee, The Ohio State University.

TABLE 1

Weight, Spleen Relative Weight (SRW), Hematocrit and Hemoglobin of Fish Treated by Immersion

| Treatment | Final weight (mean ± SD) | SRW[1] (% body weight) | Hematocrit (%) | Hemoglobin (g/100 mlk) |
|---|---|---|---|---|
| Control | 22.0 ± 1.90 | 0.080 ± 0.015 [ab] | 37.8 ± 3.51 | 8.47 ± 1.09 |
| E-22 | 22.4 ± 1.36 | 0.082 ± 0.012 [a] | 36.2 ± 2.57 | 8.39 ± 0.85 |
| CP57 | 21.5 ± 1.14 | 0.097 ± 0.004 [a] | 36.5 ± 1.50 | 7.66 ± 0.31 |
| 2137 | 21.8 ± 1.34 | 0.082 ± 0.004 [a] | 35.2 ± 2.25 | 7.84 ± 0.77 |

[1]Spleen relative weight (spleen wt. × 100/body wt) was measured after 9 weeks. All other values were measured after 7 weeks.
[2]Values (±SD) having different superscripts are significantly different ($P < 0.05$)

The fish growth and physiological parameter values in the table above show that there were no significant differences in growth rate (final weight), hematocrit, and hemoglobin among all the treatment groups ($P>0.05$).

Example 3

Feed Pellet

Transgenic *Chlamydomonas reinhardtii* expressing the P57 protein from *Rennibacterium salmoninarum* as a fusion protein on the plasma membrane (called E-22 algae) or in the chloroplast (called CP57 algae) were prepared as described in Example 1.

The algae were grown in TAP medium as described above in Example 2 to a density of $1\times10^6$ cells/ml. The algal cells were harvested by centrifugation, frozen in liquid nitrogen and freeze-dried.

Three semi-purified diets formulated based on casein-gelatin as a protein source were used for oral administration. The three semi-purified diets were isonitrogenous and isocaloric to incorporate 4% (on dry weight basis) of three different types of algae. The three algae were E-22, CP57, and CC-2137. Five percent of fish protein concentrate (CPSP 90, Sopropeche S. A., Boulogne-Sur-Mer, France) was supplemented into the diets to enhance their palatability. The dietary ingredients were mixed with distilled water and cold-pelleted into 2.0 mm diameter size, and then freeze-dried to have less than 5% moisture. Diets were crushed and sieved into a desirable particle size (0.8-2.0 mm), and stored at −20° C. until use.

Rainbow trout juveniles (average initial weight, 9.1±0.5 g) were randomly distributed into 24 rectangular tanks (20 L capacity) at a density of 22 fish per tank, 3 tanks per dietary treatment. A control group was also used (each in triplicate tanks) and were fed a commercial diet (Bioproducts, Inc. Oregon). The control group was not exposed to any disturbances. Each experimental diet was fed to a group (3 tanks) of fish at the feeding rate of 2% of fish body weight for 3 consecutive days. Accordingly, the results in an approximate intake of 25 mg of algae protein/100 g fish body weight/day. After 3 days of feeding algae diets twice a day, all the fish groups were fed with the same commercial diet for 3 weeks (2.5% per day), twice per day, 7 days per week. The $2^{nd}$ oral treatment (boost) was conducted again with the same algae diets and the commercial diet at the feeding rate of 2% of fish body weight for 4 days. After the 4 days of the $2^{nd}$ oral treatment, all the fish groups were fed the same commercial diet for 4 weeks until the second sampling in this experiment. The fish were kept for 2 additional weeks at the feeding rate of 1.5% of fish weight and sampled again (third sampling; 9 weeks).

TABLE 2

Weight, Spleen Relative Weight (SRW), Hematocrit and Hemoglobin of Fish Treated Orally

| Treatment | Final weight (mean ± SD) | SRW[1] (% body weight) | Hematocrit (%) | Hemoglobin (g/100 mlk) |
|---|---|---|---|---|
| Control | 19.9 ± 0.60 | 0.093 ± 0.004 [a] | 38.3 ± 5.69 | 9.52 ± 0.96 |
| E-22 | 21.5 ± 1.00 | 0.053 ± 0.001 [c] | 38.5 ± 1.80 | 8.40 ± 0.83 |
| CP57 | 22.0 ± 0.12 | 0.056 ± 0.004 [bc] | 39.5 ± 3.12 | 8.34 ± 0.62 |
| 2137 | 20.6 ± 0.66 | 0.052 ± 0.003 [c] | 35.3 ± 0.58 | 7.61 ± 0.02 |

[1]Spleen relative weight (spleen wt. × 100/body wt) was measured after 9 weeks. All other values were measured after 7 weeks.
[2]Values (±SD) having different superscripts are significantly different (P < 0.05)

The fish growth and physiological parameter values in the able above show that there were no significant differences in growth rate (final weight), hematocrit, and hemoglobin among all the treatment groups (P>0.05). Spleen relative weight (SRW) was significantly lower in orally treated fish groups than in a control fish group and all the fish groups in immersion treatments (P<0.05).

Example 4

Serum and Mucus Antibodies in Fish after Administration of Algae

Serum and mucus obtained from the fish treated by the immersion method (Example 2) as well as the oral feeding method (Example 3) were examined for the presence of antibodies reactive with the P57 immunogens expressed by the transgenic algae. This was done by using the serum or the mucus from fish fed CP57, E-22, CC-2137, or no algae to probe western blot membranes to which were transferred proteins from SDS-PAGE gels of solubilized wild-type *Chlamydomonas* cells or transgenic *Chlamydomonas* expressing the P57 protein in the chloroplast (CP57), or as a fusion protein between the high $CO_2$ induced protein and the P57 antigenic determinant (E-22).

Wild-type, E-22 and CP57 algae were boiled in SDS-PAGE loading buffer for 5 minutes. Samples were loaded at 15 µg chlorophyll per well (see Arnon D (1949), Plant Physiol. 24: 1-15, for additional information on chlorophyll assays) on a 12.5% acrylamide gel with a 6% acrylamide stacking gel. The samples were electrophoresed at 15-18 mAmp constant current for 5-6 hr. Following electrophoresis the proteins were transferred from the gel to immobilon-P (PVDF=Volyvinylidene fluoride) membrane using a semi-dry system at 1.25 mA per square centimeter of membrane for 2-3 hr. After removing the membrane from semi-dry electroblotter, the membrane was soaked in methanol for 15 second and dried at room temperature for 30 minutes. The membrane was then washed twice with PBST buffer (10 mM Sodium phosphate, 150 mM NaCl, 1% Tween-20, pH 7.4) for 5 minute each. (0.25 mL PBST per square centimeter of membrane) and blocked with 3% casein (in PBST buffer) at 0.25 mL per square centimeter for 1-2 hr. The membrane was then washed twice with PBST buffer (10 mM Sodium phosphate, 150 mM NaCl, 1% Tween-20, pH 7.4) for 5 minute each. (0.25 mL PBST per square centimeter membrane).

All fish mucus and serum were treated with soluble protein from CC-425 algal strain at 1:2 (vol/vol ratio) for 1 hr at room temperature followed by centrifugation to remove non-specifically bound proteins. Fish mucus or sera was used at a 1:150 dilution in 1% BSA in PBST and incubated at room temperature for 2 hr (used 0.1 mL of serum or mucus solution in buffer per square centimeter of blotting membrane). The membrane was then washed twice with PBST buffer (10 mM sodium phosphate, 150 mM NaCl, 1% Tween-20, pH 7.4) for 5 minute each (0.25 mL PBST per square centimeter of membrane). This was followed by incubation with mouse anti IgM Rainbow trout serum (1:200 dilution in 1% bovine serum albumin (BSA) in PBST) at room temperature for 2 hr (0.1 mL dilution buffer per square centimeter of membrane). The membrane was then washed twice with PBST buffer for 5 minute each (0.25 mL PBST per square centimeter of membrane) followed by incubation with goat anti-mouse antisera conjugated to horseradish peroxidase (HRP) at a 1:3,000 dilution in 1% BSA in PBST at room temperature for 1 hr (0.25 mL dilution buffer per square centimeter of membrane). The membrane was then washed twice with PBST buffer for 5 minute each. (0.25 mL PBST per square centimeter of membrane). The HRP detection system was Opti-4CN Substrate Kit from Bio-Rad. Opti-4CN is an improved and more sensitive version of the calorimetric horseradish peroxidase (BRP) substrate, 4-chloro-1-naphthol (4CN). Normally, this step takes time about 20-30 minutes (0.25 mL substrate per square centimeter of membrane).

Figure 4:
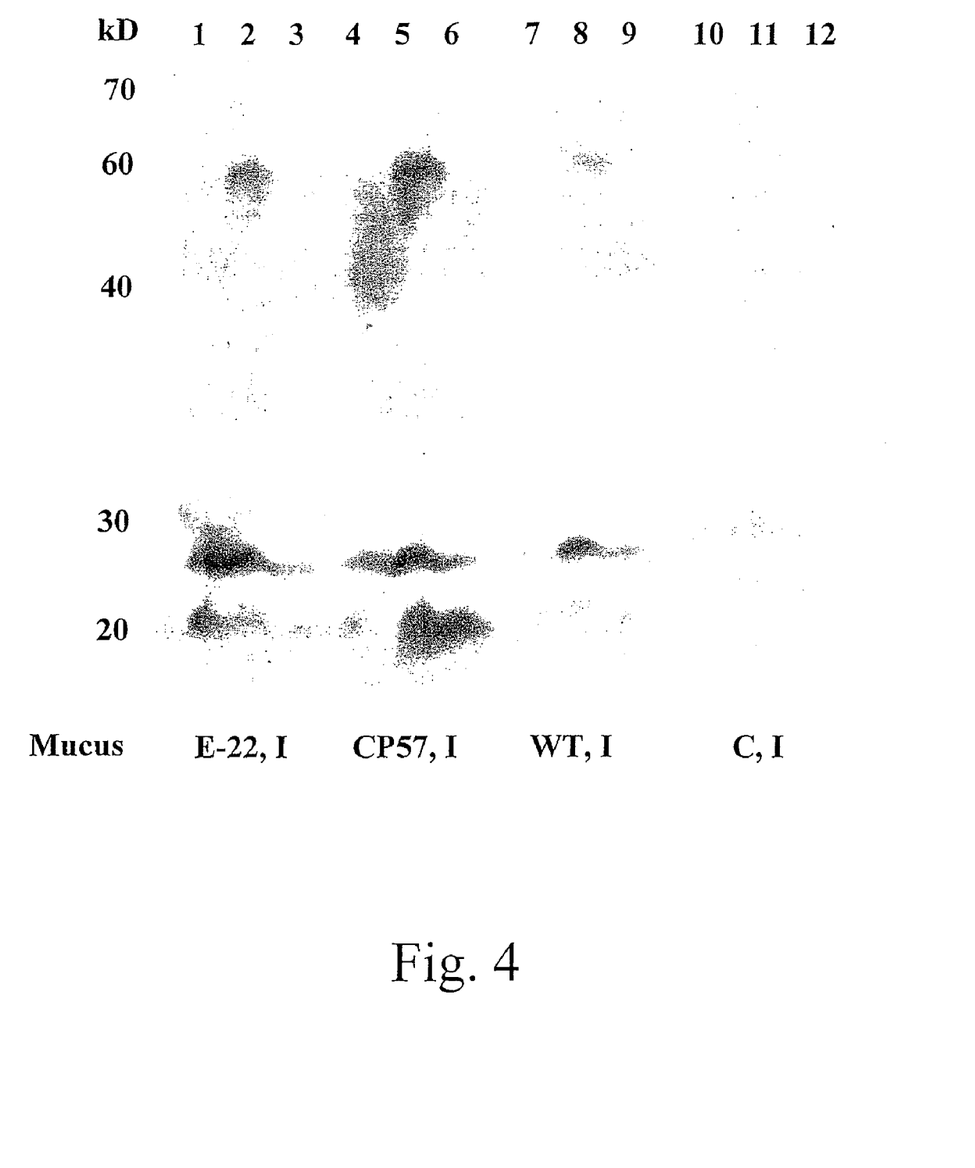
FIG. 4 is a western blot of trout sera probed against algal cells used for oral immunization. Lane 1: E-22; Lane 2: CP57; Lane 3: CC-2137(WT); Lane 4: E-22; Lane 5: CP57; Lane 6: CC-2137(WT); Lane 7: E-22; Lane 8: CP57; Lane 9: CC-2137(WT); Lane 10: E-22; Lane 11: CP-57; Lane 12: CC-2137(WT)
Figure 5:
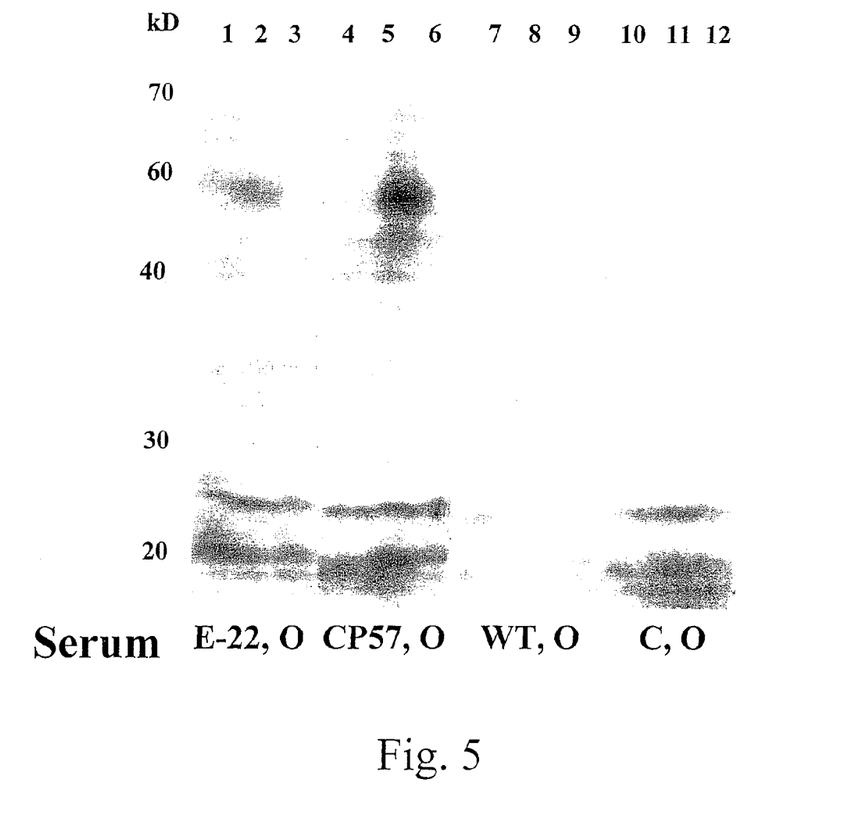
FIG. 5 is a western blot of Trout Mucus Probed Against Algal Cells used for Immersion Immunization. Lane 1: E-22; Lane 2: CP57; Lane 3: CC-2137(WT); Lane 4: E-22; Lane 5: CP57; Lane 6: CC-2137(WT); Lane 7: E-22; Lane 8: CP57; Lane 9: CC-2137(WT); Lane 10: E-22; Lane 11: CP-57; Lane 12: CC-2137(WT)

The results of the studies are shown in FIG. 4 which shows sera from fish that were fed algae in their diet, and in FIG. 5 which shows mucus from fish that were immersed in algae.

The first western blot (FIG. 4) shows that sera from fish fed pellets containing either E-22 or CP57 algae recognized a 57 kD protein present in algae (CP57) expressing the P57 protein in the chloroplast (lanes 2 and 5). Significantly, no 57 kD band was detected when using sera from fish fed either wild type or no algae in the diet. In addition, two protein bands were detected at 22 and 27 kD in all serum treatments. These bands arise from non-specific interactions. In contrast, no 57 kD proteins were detected in serum from fish that were immersed in either E-22, CP57, wild-type or no algae. These results indicate that fish fed food containing transgenic algae expressing the P57 protein of *Rennibacterium salmoninarum* generated specific antibodies against the P57 protein. Unfortunately, due the cross-contaminating band at 22 kD it was not possible to determine whether fish fed pellets containing E-22 algae generated antibodies against the 22 kD fusion protein. However, the fact that the P57 protein present in CP57 algae was detected using sera from E-22 fed fish suggests that the 22 kD fusion protein was immunogenic against the P57 antigenic determinant present in the fusion protein.

In addition, fish mucus was tested for the presence of antibodies generated against the P57 protein. As shown in FIG. 5, western blots probed with mucus from fish immersed in E-22 and CP57 algae was immunoreactive against the P57 protein present in CP57 algae (lanes 2 and 5). Again no immune reaction was observed using mucus from fish immersed in wild-type or no algae. These results demonstrate that P57-specific antibodies were expressed in mucus of fish immersed in E-22 and/or CP57 algae. There also appears to be an immune reaction specific for the 22 kD fusion protein when using mucus from fish immersed in E-22 algae (lane 1). However, this result is tentative since a non-specific interaction is observed at the same molecular weight in lanes 5 and 6. Significantly, immersion of fish with any algal strain failed to generate P57-specific antibodies in sera. Overall, these results indicate that immersion with algae expressing foreign and immunogenic proteins (P57) is an effective means to generate the production of protective antibodies in the mucus of fish.

Example 5

Algae Expressing WSSV Proteins and Administration to Shrimp

White Spot Syndrome Virus (WSSV) is a cause of disease of shrimp. Shrimp production losses of 80% due to WSSV infection have been reported and shrimp farms can be shut down for periods of up to two years following a WSSV infestation.

VP28, VP26, VP24, and VP19 are known proteins from WSSV (PCT Int. Appl. No. WO 0109340). Using gene specific primers, each of the four known viral proteins is amplified using WSSV DNA as a template (van Hulten, et al., 2001, PCT International Publication WO 0109340). Each of these genes is cloned separately and together into a *Chlamydomonas* expression vector similar to the methods described in Example 1. For example the pSSCR7 plasmid which drives high-level expression in the cytoplasm, and the pSSCR7 vector having a 5' aryl sulfatase periplasmic targeting transit sequence (Davies et al., 1994, Plant Cell 6: 53-63). The aforementioned vectors randomly integrate into the *Chlamydomonas* nuclear genome. In addition, a proprietary chloroplast transformation vector that integrates into the chloroplast genome by homologous recombination can be used (Hutchison, et al., 1996, Chapter 9, Chloroplast transformation. Pgs. 180-196; In: Molecular Genetics of Photosynthesis, Frontiers in Molecular Biology. Anderson B., Salter, A H, and Barber J. eds.; Oxford University Press). Each of these vectors contains promoters that drive high levels of expression in the cytoplasm or chloroplast. Viral protein expression is quantified by western blot analysis normalized against known loadings of WSSV (see objective 1A4 for quantification of WSSV). For the western blot analysis polyclonal antibodies are generated against WSSV proteins by injection of purified and heat-denatured WSSV into rabbits.

The various expression systems are used to determine which pattern of expression (periplasmic, cytoplasmic or chloroplast) most effectively induces the shrimp "immune-response" (Bachere, 2000, Aquaculture 191: 3-11; Rombout et al., 1985, Cell Tissue Res. 239: 519-30). While periplasmic expressed viral proteins are expected most effective, they are potentially most vulnerable to digestion cytoplasmic and chloroplast expressed proteins would be progressively less susceptible to digestion (D'Souza, et al., 1999, Marine Biol. 133: 621-633).

PSF (pathogenic specific free) shrimp larvae are fed either wild-type or VP-expressing microalgae 3-5 days prior to challenge with known titers of WSSV. During the WSSV challenge, the shrimp larvae are fed the appropriate algal strain either as live algae or as dried algae in feed pellets (D'Souza, et al., 1999, Marine Biol. 133: 621-633). Various concentrations of algae feed are compared. Relative percent survival will be calculated during the weeks following WSSV exposure for all treatments. As described below, molecular markers specific for shrimp disease inducible genes will be used in quantitative real time-PCR experiments to evaluate the "immune" response in shrimp prior to and after exposure to 1) WSSV VP expressing algae, 2) wild type algae, 3) WSSV VP expressing algae followed by WSSV exposure, 4) WSSV alone, and 4) no algae or WSSV. Based on studies with injected WSSV proteins (van Hulten, et al., 2001, PCT International Publication WO 0109340) it is expected that shrimp fed microalgae expressing WSSV VP proteins will be protected from WSSV infection.

Example 6

Rabbits

Transgenic algae expressing antigenic proteins (in the chloroplast, cytoplasm, or on the cell surface as fusion proteins) are delivered to rabbits as a component of the feed pellets, essentially as described above for fish. Alternatively, the algae are delivered as mixed with the drinking water. The transgenic algae may, for example, express the CS6 and Vi antigens of *Salmonella typhi*.

Although the invention has been described in detail with reference to certain preferred embodiments, variations and modifications exist within the scope and spirit of the invention as described and defined in the following claims.

The invention claimed is:

1. A method for delivering antigens to a host animal to induce an immune response in the host animal, the method comprising the steps of
administering an immunogenic composition to the host animal wherein the composition comprises a photosynthetically disabled algal cell transformed by an expression vector, wherein the expression vector comprises a nucleotide sequence coding for an antigen comprising a holoprotein or protein fragment from a microorganism selected from the group consisting of a bacterium, a virus, a fungus, and a parasite, and
inducing the immune response in the host animal.

2. The method of claim 1, wherein the expression vector further comprises a promoter operably linked to the nucleotide sequence coding for the antigen.

3. The method of claim 2, wherein the expression vector further comprises a terminator for terminating transcription.

4. The method of claim 3, wherein the algal cell expresses the antigen in an area selected from the group consisting of nucleus, chloroplast, mitochondria, periplasmic space, cell membrane, cytoplasm, and cell wall.

5. The method of claim 1, wherein the algal cell is selected from the group consisting of green algae, brown algae, and diatoms.

6. The method of claim 1 wherein the algal cell is *Chlamydomonas reinhardtii*.

7. The method of claim 1 wherein the antigen is part of a fusion protein.

8. The method of claim 3 wherein the algal cell is *Chlamydomonas reinhardtii*.

9. The method of claim 1 wherein the algal cell is packaged as a food product.

10. The method of claim 9 wherein the food product is a capsule.

11. The method of claim 1 wherein multiple algal cells are incorporated into a pellet.

12. The method of claim 11 wherein the algal cells are selected from the group consisting of living and dead cells.

13. The method of claim 1 wherein the algal cell is suspended in water for immersing the host animal.

14. The method of claim 13 wherein the algal cell is dried and formed into a powder prior to being suspended in water.

15. The method of claim 1 wherein the algal cell is mixed with a liquid and packaged as a drink.

16. The method of claim 1, wherein the expression vector further comprises a 5' psbA promoter and a 3' psbA terminator, and wherein the nucleotide sequence coding for the antigen is positioned between the 5' psbA promoter and the 3' psbA terminator and is operably linked to the 5' psbA promoter.

17. The method of claim 1 wherein the nucleotide sequence coding for the antigen is fused to an end of the low $CO_2$-induced plasma membrane protein gene.

18. The method of claim 1 wherein the expression vector is incorporated into genetic material selected from the group consisting of nuclear, chloroplast, and mitochondrial.

19. The method of claim 1 wherein the algal cell is delivered by oral administration.

20. The method of claim 1 wherein the animal is selected from the group consisting of mammals, fish, birds, and crustaceans.

21. The method of claim 20 wherein the algal cell is delivered by oral administration.

22. The method of claim 20, wherein the animal is a fish or a crustacean and the algal cell is suspended in water for immersing the host animal.

\* \* \* \* \*